United States Patent [19]

Bauer

[11] Patent Number: 5,030,631
[45] Date of Patent: Jul. 9, 1991

[54] TRICYLCLIC ARYLSULFONAMIDES

[75] Inventor: Barr E. Bauer, Elmwood Park, N.J.

[73] Assignee: Schering Corporation, Kenilworth, N.J.

[21] Appl. No.: 441,501

[22] Filed: Nov. 27, 1989

[51] Int. Cl.$^5$ ............... C07D 243/02; C07D 243/04; C07D 243/08; A61K 31/55

[52] U.S. Cl. .................................. 514/218; 540/470; 540/553; 540/575; 544/361; 544/380; 546/80; 546/81; 546/102; 546/103; 546/108; 546/111; 564/86; 564/88; 564/89

[58] Field of Search ............... 540/553, 575; 514/218

[56] References Cited

PUBLICATIONS

Grisar et al., Journal of Medicinal Chemistry (1974), vol. 17, No. 8, pp. 890-893.
Chem. Abstracts, 1983, 98:55684e, Pigment Compositions.
Chem. Abstracts, 1983, 98:17357r, Contrasting Actions of Amino Acids, etc.
Chem Abstracts, 1985, 102:148384y, Effect of Molecular Structure on Optical Properties, etc.
Chem. Abstracts, 1985, 103:47835m, Antiulcer Activity of Dehydroabietic Acid Derivatives.
Chem. Abstracts, 1985, 103:5923h, Preparation, Structure and Asymmetric Diols—Alder Reactions.
Chem Abstracts, 1984, 101:210744a, Monosulfonylquinone Derivatives.
Chem. Abstracts, 1982, 96:8114t, Syntheses of Cationic Dyes with Anthraquinone Structure.
Chem. Abstracts, 1987, 106:32490h, Some New Amides and Sulfonamides and Their Biological Activity.
Chem. Abstracts, 110:17861u, 1987, TLC of Some Derivatives of Fluorene.
Chem. Abstracts, 110:110129w, Herbicidal Aryltriazolines, 1988.
Chem. Abstracts, 95:150247m, 1980, Synthesis and Properties of Arenesulfinic Acids.
Chem. Abstracts, 1976, 84:24462n, Spirit-Reproducing Carbon Papers.
Chem. Abstracts, 1976, 84:135936q, Steroidal Sulphur Compounds, Part XII.
Chem. Abstracts, 1975, 83:146981f, Stereoselective Formation of Some Thietanel,1-dioxides.
Chem. Abstracts, 1975, 83:108314h, Syntheses of Amino Acid Derivatives and Their Biological Activities.
Chem. Abstracts. 1975. 82;170568b, Complexes in Acylation and Sulfonation, etc.
Chem. Abstracts, 1981, 94:191989c, Studies on the Synthesis and Properties of Arenesulfinic Acids.
Chem. Abstracts, 1980, 93:197554h, Thrombin Inhibitors.
Chem. Abstracts, 1980, 93:10680c, Thrombin Inhibitors.
Chem. Abstracts, 1980, 93:168614x, N-(2-Fluorenylsulfonyl) Amino Acids.
Chem. Abstracts, 1980, 92:198165y, Sulfur-Containing Fluorenyl and Phenanthryl Derivatives.
Chem. Abstracts, 1978, 89:188945b, Color Diffusion--Transfer Photographic Materials.
Chem. Abstracts, 90:64360h, 1978, Dye-Releasing Red X Compounds for Diffusion-Transfer Color Photographic Materials.
Chem. Abstracts, 1979, 152610v, N-Arylaulfonyl-Argininamides.
Chem. Abstracts, 88:51165g, 1977, Pharmaceutical N-Sulfonylaminocarboxylic Acids.
Chem. Abstracts, 87:102096z, 1977, The Reactions of Aryldiazomethanes with Sulfur Dioxide in the Presence of Enamines.
Chem. Abstracts, 87:39158d, 1975, Synthesis and Properties of Arylsulfinic Acids.
Chem. Abstracts, 87:53578x, 1977, Aminoacyl Derivatives of Nucleosides, Nucleotides, and Polynucleotides.
Chem. Abstracts, 83639r, 1973, N-2-Fluorenesulfonylamino Acids.
Chem. Abstracts, 420p, 1973, Synthesis of Antimicrobial Nitroimidazolyl 2-Sulfides, etc.
Chem. Abstracts, 13464K, 1973, Dual Effect in the Mechanism of Action of Antiinfluenza Virus Amino Acid Analogs.
Chem. Abstracts, 92427b, 1973, Synthesis of N-Substituted 6-Sulfonamides of Methyl Dehydroabietate etc.
Chem. Abstracts, 87403m, 1972, Inhibitory Effect of Antiviral Drugs on Viral-Specific Inflammatory Factors Produced Influenza Virus.
Chem. Abstracts, 87402k, 1072, Chemotherapeutic Effect of New Amino Acid Analogs on Influenza.
Chem. Abstracts, 17622n, 1972, Disperse Anthraquinone Dyes.
Chem. Abstracts, 136657n, 1973, Antiviral, Antiinflammatory, and Antitumoral N-Substituted Amino Acids.
Chem. Abstracts, 1973, 78:17621m, Anthraquinone Dyes.
Chem. Abstracts, 1971, 75:21010s, Antiviral N-Acyl-, Sulfonyl-, and Alkylamino Acids.
Chem. Abstracts, 106997f, 1973, Organotin Wood Preservatives.
Chem Abstracts, vol. 72, 1970, 31497h, Influence of Molecular Structure on the Optical Properties of Sulfoxide Systems.

(List continued on next page.)

*Primary Examiner*—Mukund J. Shah
*Assistant Examiner*—Philip I. Dalton
*Attorney, Agent, or Firm*—Joseph T. Majka; James R. Nelson

[57] ABSTRACT

Novel tricyclic arylsulfonamides useful for treating hypertension and bronchoconstiction, as well as to their pharmaceutical compositions and methods for using the same.

13 Claims, No Drawings

OTHER PUBLICATIONS

Chem. Abstracts, 32697b, 1970, Anthraquinone Disperse Dyes.
Chem. Abstracts, 96215k, 1966, Anthraquinone Dyes.
Chem. Abstracts, 1083, 107:154053j, Synthesis of Arylsulfinic Acids.
Chem. Abstracts, 107:15599d, 1986, Photosensitive Compositions for Fine Patterning.
Chem. Abstracts, 108:218182f, 1988, A Predicted Tertiary Structure of a Thrombin Inhibitor-Trypsin Complex Explains Mechanisms.
Chem. Abstracts, 1988, 109:110883s, Mild Reductive Cleavage of the 9-Anthracenesul Fonamido Function.
Chem. Abstracts, vol. 67, 1967, 43638q, Chemistry of Sulfines, III, Further Investigations on the Preparation.
Chem. Abstracts, vol. 67, 1967, 2611g, Reactions of P-Ylides with Sulfenes.
Chem. Abstracts, 22916w, 1967, Water-Insoluble Anthraquinone Dyes.
Chem. Abstracts, 70376s, 1969, Optical Properties-Molecular Structure Relation in Sulfoxide Systems.
Chem. Abstracts, 1977, 86:30073u, Amino Acid Derivatives.
Chem. Abstracts, 1986, 105:115398q, Peptide Synthesis by Prior Thiol Capture.
Chem. Abstracts, 1986, 105:226588w, 1,2,4-Thiadiazole Derivatives.
Chem. Abstracts, 1986, 105:235893u, Base Presursors for Thermal Recording and Photothermographic Materials.
Chem. Abstracts, 1986, 105:97950g, Lysine Derivative and Proteinase Inhibitor.
Chem. Abstracts, 1986, 105:60939j, Arginine Derivatives and Their Therapeutic Use.
Chem. Abstracts, 1986, 105:6292e, Effect of Molecular Structure on Optical Properties of Systems Containing Carbon Chirality Centers, Part XXX.
Chem. Abstracts, 1989, 111:25008g, Dispersants for Pigments.
Chem. Abstracts, 1977, 86:173065d, Anthraquinone Dyes.

TRICYLCLIC ARYLSULFONAMIDES

FIELD OF THE INVENTION

The present invention relates to novel tricyclic arylsulfonamides useful for treating hypertension and bronchoconstriction, as well as to their pharmaceutical compositions and methods for using the same.

BACKGROUND

Numerous references teach bicyclic arylsulfonamides useful as anti-hypertensive agents such as disclosed in U.S. Pat. Nos. 4,857,301 and 4,634,770. However, art which teaches the treatment of hypertension employing tricyclic arylsulfonamides is relatively sparse. Japanese Kokai Tokkyo Koho JP No. 63,305,173(88,305,173) 13 Dec. 1988, Appl. No. 87/140,924, 05 June 1987 teaches certain tricyclic arylsulfonamides useful as pigment dispersants. There is a need to develop new and improved compounds useful in the treatment of hypertension which have not been discovered.

SUMMARY OF THE INVENTION

The present invention is directed toward compounds useful in the treatment of hypertension of the formula:

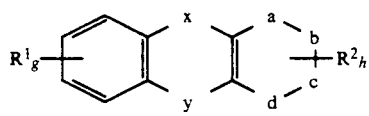

and

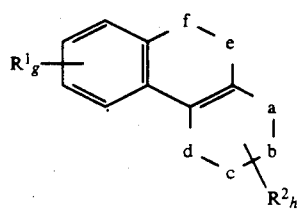

or a pharmaceutically acceptable salt or solvate thereof, wherein $R^1$ and $R^2$ independently represents hydrogen, halogen, alkyl, hydroxyl, amino, alkenyl, substituted alkenyl, alkynyl, substituted alkynyl, aryl, substituted aryl, aralkyl, substituted aralkyl, heteroaryl, substituted heteroaryl, heteroaralkyl or substituted heteroaralkyl;

g and h independently represent 0, 1, 2, 3 or 4;

a, b, c, d, e, f, x and y independently represent —C= or —N= and x and y can further independently represent —O—, —S—, —NR$^{20}$— wherein $R^{20}$ represents hydrogen or alkyl, —CO—, —(CR$^3$R$^4$)$_w$— or —(CR$^5$R$^6$)$_z$— wherein w and z can independently represent integers from zero to 8 inclusive and w+z is an integer from zero to 8 inclusive, and $R^3$, $R^4$, $R^5$ and $R^6$ independently represent
H,
alkyl,
substituted alkyl,
halogen,
—OH,
alkoxy,
thiol,
—COOH or salts, amides or esters thereof,
—NH$_2$, —NHR$^{31}$, —NR$^{31}$R$^{32}$ or —N$^+$R$^{31}$R$^{32}$R$^{33}$ wherein $R^{31}$R$^{32}$ and $R^{33}$ independently represent hydrogen or alkyl,
alkenyl,
alkynyl,
aryl,
aralkyl,
heteroaryl,
heteroaralkyl,
—COR$^{31}$ wherein $R^{31}$ is defined hereinbefore,
—C(=NH)NR$^{31}$R$^{32}$ or salts thereof, wherein $R^{31}$ and $R^{32}$ are as defined hereinbefore;

wherein at least one of a, b, c, d, e, f, x or y is

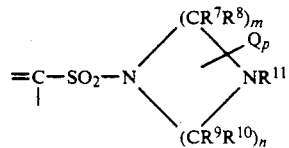

or

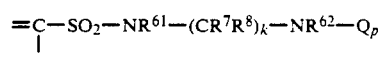

wherein $R^7$, $R^8$, $R^9$ and $R^{10}$ independently represent any of the values for $R^3$, $R^4$, $R^5$ and $R^6$, and m and n independently represent an integer from 2 to 8 inclusive, such that the sum of m+n=an integer from 4 to 14 inclusive;

k can be an integer from 2 to 14 inclusive;

p can be zero or one;

$R^{61}$ and $R^{62}$ independently represent hydrogen, alkyl or substituted alkyl; and Q can be substituted for $R^{11}$ on the ring nitrogen or on the acylic nitrogen, or for any of $R^7$, $R^8$, $R^9$ or $R^{10}$ on the ring carbon, and can represent

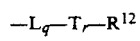

wherein

L represents —CO—, —COO—, —CONR$^{21}$—, or —SO$_2$NR$^{21}$— wherein $R^{21}$ represents hydrogen or alkyl and q represents zero or one;

T represents a disubstituted unbranched or branched alkyl chain of zero to 10 carbon atoms which can optionally contain 1, 2 or 3 unsaturated bonds, disubstituted cycloalkyl of 3 to 10 carbon atoms, disubstituted cycloalkenyl of 3 to 10 atoms containing 1 or 2 unsaturated bonds, or disubstituted aryl, and r represents zero or one, and $R^{11}$ and $R^{12}$ independently represent any of the values for $R^3$, $R^4$, $R^5$, $R^6$, $R^7$, $R^8$ and $R^9$.

The compounds of formulas XIII and XIV are useful as kinase inhibitors, antibronchoconstrictors and antihypertensive agents. Kinase is an enzyme that catalyzes the transfer of phosphate groups from adenosine triphosphate (ATP) or adenosine diphosphate (ADP) to a substrate.

A preferred group of compounds derived from formulas XIII and XIV are of formulas XIIIi and XIVi:

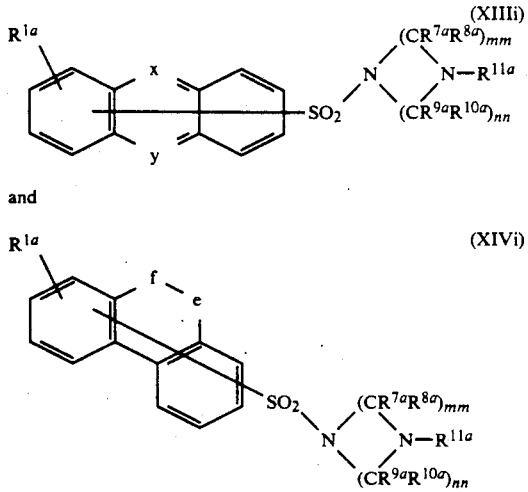

wherein $R^{1a}$ represents hydrogen or halogen, preferably bromo, e, f, x and y independently represent —C=, —N=, —(CR$^{3a}$R$^{4a}$)$_w$— or —(CR$^{5a}$R$^{6a}$)$_z$— wherein $R^{3a}$, $R^{4a}$, $R^{5a}$ and $R^{6a}$ independently represent hydrogen or alkyl, preferably hydrogen or methyl, and w and z independently represent 0, 1 or 2 and the sum of w+z=1 or 2; and $R^{7a}$, $R^{8a}$, $R^{9a}$ and $R^{10a}$ independently represent hydrogen or alkyl, preferably hydrogen, mm and nn independently represent 2, 3 or 4 and mm+nn=4, 5 or 6 and $R^{11a}$ represents hydrogen, —COR$^{31a}$ and —C(=NH)NR$^{31a}$R$^{32a}$ wherein $R^{31a}$ and $R^{32a}$ independently represent hydrogen or alkyl, preferably hydrogen.

The present invention is also directed toward an antihypertensive pharmaceutical composition containing an antihypertensive amount of a compound of formula XIII or XIV in a pharmaceutically acceptable carrier. The present invention is also directed to a method for treating hypertension in a mammal comprising administering to a mammal in need of such treatment an antihypertensive effective amount of a compound of formula XIII or XIV.

DETAILED DESCRIPTION OF THE INVENTION

As used herein, unless otherwise stated, the term "alkyl" refers to a straight chain saturated hydrocarbon moiety containing from 1 to 20 carbon atoms, preferably one to six carbon atoms or a branched saturated hydrocarbon moiety of 3 to 20 carbon atoms, such as for example, methyl (i.e. —CH$_3$), ethyl, propyl, isopropyl, butyl, isobutyl, tert-butyl, pentyl, hexyl and the like; the term "substituted alkyl" refers to an alkyl moiety which is further substituted at at least one of alkyl carbons by one or more of the following groups: halo (i.e. haloalkyl), alkyl of one to 20 carbon atoms, aryl of six to fourteen carbon atoms, cyano (i.e. —CN), carboxyl (i.e. —COOH) or salts, amides or esters thereof, thiol (i.e. —SH), nitro (i.e. —NO$_2$) and hydroxyl (i.e. —OH);

the term "alkenyl" refers to a straight chain hydrocarbon moiety of two to 20 carbon atoms or a branched hydrocarbon moiety of three to 20 carbon atoms having at least one carbon to carbon double bond such as allyl, ethenyl, propenyl, 1-butenyl, 2-butenyl, isobutenyl, 1-pentenyl, 2-methyl-1-butenyl, 1-hexenyl and the like; the term "substituted alkenyl" refers to an alkenyl moiety which is further substituted at at least one of the alkenyl carbons by one or more of the following groups: halo, alkyl of one to 20 carbon atoms, aryl of six to fourteen carbon atoms, cyano, carboxyl or salts, amides or esters thereof, thiol, nitro and hydroxyl;

the term "alkynyl" refers to a straight chain hydrocarbon moiety of two to 20 carbon atoms or a branched hydrocarbon moiety of three to 20 carbon atoms having at least one carbon to carbon triple bond;

the term "alkoxy" refers to an alkyl moiety of one to 20 carbon atoms covalently bonded to an adjacent structural element through an oxygen atom, as for example, methoxy, ethoxy, propoxy, butoxy, pentoxy, hexoxy and the like.

the term "aryl" refers to a carbocyclic moiety containing at least one benzenoid-type ring, with the aryl groups preferably containing from 6 to 14 carbon atoms, for example, phenyl, naphthyl, indenyl, indanyl and the like; the term "substituted aryl" refers to an aryl moiety which is further substituted at the carbon by one or more of the following groups: halo, alkyl of one to 20 carbon atoms, aryl of six to fourteen carbon atoms, cyano, carboxyl or salts, amides or esters thereof, thiol, nitro and hydroxyl;

the term "aralkyl" refers to an aryl moiety of six to 14 carbon atoms covalently bonded to an alkyl moiety of one to 20 carbon atoms, for example, benzyl, phenylethyl, and the like; the term "substituted aralkyl" refer to an aralkyl moiety which is further substituted at at least one of the aralkyl carbons by one or more of the following groups: halo, alkyl of one to 20 carbon atoms, aryl of six to fourteen carbon atoms, cyano, carboxyl or salts, amides or esters thereof, thiol, nitro and hydroxyl;

the term "heteroaryl" refers to a cyclic moiety having at least one oxygen (O), sulfur (S) and/or nitrogen (N) heteroatom interrupting the ring structure and having a sufficient number of unsaturated carbon to carbon bonds, nitrogen to carbon bonds, and the like, to provide aromatic character, with the heteroaryl groups preferably containing from 2 to 13 carbon atoms, for example, 2-, 3- or 4-pyridyl, 2- or 3-furyl, 2- or 3-thienyl, 2-, 4- or 5-thioazolyl, 2-, 4- or 5-imidazolyl, 2-, 4- or 5-pyrimidinyl, 2-pyrazinyl, 3- or 4-pyridazinyl, 3-, 5- or 6[1,2,4-triazinyl], 3- or 5-[1,2,4-thiadiazolyl], 2-, 3-, 4-, 5-, 6- or 7-benzofuranyl, 2-, 3-, 4-, 5-, 6- or 7-indolyl, 3-, 4- or 5-pyrazolyl, 2-, 4- or 5-oxazolyl, and the like; the term "substituted heteroaryl" refers to an heteroaryl moiety which is further substituted at at least one of the heteroaryl carbons or heteroatoms by one or more of the following groups: halo, alkyl of one to 20 carbon atoms, aryl of six to fourteen carbon atoms, cyano, carboxyl or salts, amides or esters thereof, nitro and hydroxyl;

the term "heteroaralkyl" refers to a heteroaryl moiety of 2 to 13 carbon atoms as defined hereinbefore, covalently bonded to an alkyl moiety of one to 20 carbon atoms; the term "substituted heteroaralkyl" refer to a heteroaralkyl moiety which is further substituted at at least one of the heteroaralkyl carbons or heteroatoms by one or more of the following groups: halo, alkyl of one to 20 carbon atoms, aryl of six to fourteen carbon atoms, cyano, carboxyl or salts thereof, nitro and hydroxyl;

the terms "halogen" and "halo" refer to fluoro, chloro, bromo or iodo;

the term "amino" refers to the moiety —NR$^{21}$NR$^{22}$ wherein $R^{21}$ and $R^{22}$ independently represent hydrogen or alkyl;

Certain compounds of this invention may exist in isomeric forms. The invention contemplates all such isomers both in pure form and in admixture, including racemic mixtures.

Certain compounds of the invention can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of the invention.

Certain compounds of the invention will be acidic in nature, e.g., those compounds which possess a carboxyl or phenolic hydroxyl group. These compounds may form pharmaceutically acceptable metal and amine salts. Examples of such metal salts are the sodium, potassium, calcium, aluminum, gold and silver salts. Examples of such amine salts are those formed with pharmaceutically acceptable amines such as ammonia, alkylamines, hydroxyalkylamines, N-methylglucamine and the like.

Certain compounds of the invention e.g., those with a basic $-NR^{31}R^{32}R^{33}$ group, also form pharmaceutically acceptable salts with organic and inorganic acids. Examples of suitable acids for such salt formation are hydrochloric, sulfuric, phosphoric, acetic, citric, oxalic, malonic, salicyclic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but both the salts and their respective free bases are suitable for purposes of this invention.

The compounds of formula XIII and XIV can be prepared according to a number of known processes whose procedures and reaction conditions can be found in J. March, Advanced Organic Chemistry, Reactions, Mechanisms, and Structure, 3rd Edition, John Wiley & Sons, New York, (1985) 1346 pages, and to the relevant references cited therein, whose preparative teaching are incorporated herein by reference.

Process A. This first procedure utilizes the following basic starting materials:

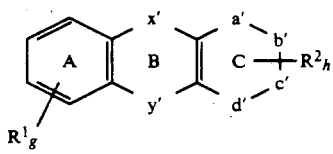

I and

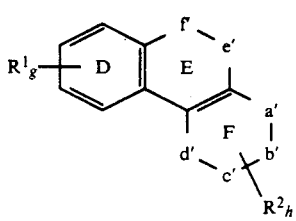

II wherein rings A, B and C in compound I and its corresponding derivatives, rings D, E and F in compound II and its corresponding derivatives are provided for identification; and $R^1$, $R^2$, g and h are as defined hereinbefore;

a', b', c', d', e', f', x' and y' independently represent $-C=$ or $-N=$; and x' and y' can further independently represent $-O-$, $-S-$, $-NR^{20}-$ wherein $R^{20}$ represents hydrogen or alkyl, $-CO-$, $-(CR^3R^4)_w-$ or $-(CR^3R^4)_z-$ wherein w and z can independently represent integers from zero to 8 inclusive and w+z is an integer from zero to 8 inclusive, and $R^3$ and $R^4$ are as defined hereinbefore. Compounds I and II can be contacted with a halogenating agent such as chlorine or bromine, optionally in the presence of iron salts, N-bromo or N-chloro succinimide, iodine in the presence of copper salts, or diazonium fluoroborates (the Schiemann Reaction) as described in March, supra, pp. 476–479 and 602–603 to give a halogenated tricyclic compound of formulas III and IV:

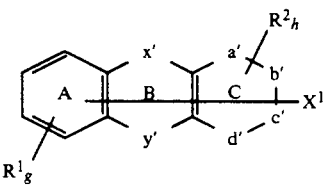

III and

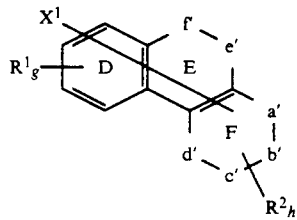

IV wherein $X^1$ is a single halogen which is inserted on any of rings A, B, C in compound III or on any of rings D, E or F in compound IV.

The halogen, $X^1$, in the compound of formulas III and IV can be replaced with a metal by contacting the compounds of formulas III and IV with a metal such as magnesium (Mg) to form a Grignard reagent, or with alkyllithium or lithium metal, as taught in J. March, supra, pp. 558–561 to give a compound of formulas V and VI:

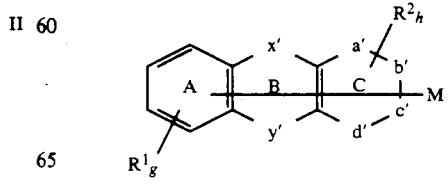

V and

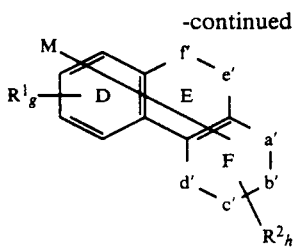

VI wherein M is Li or $MgX^1$.

The compounds of formulas V and VI can be converted to an aryl sulfinate salt by contacting the compounds of formulas V and VI with sulfur dioxide ($SO_2$). Treatment with a chlorine source such as sulfuryl chloride ($SO_2Cl_2$) or chlorine as described in March, supra, pp. 550–551 and 637 gives a sulfonyl chloride of formulas VII or VIII:

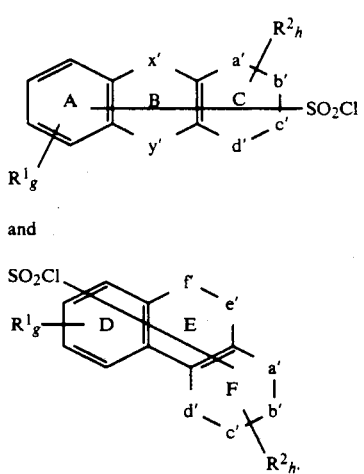

VII and

VIII

The sulfonyl chloride of formulas VII and VIII can then be contacted with a cyclic diamine (IX) or an acyclic diamine (X) of the formula

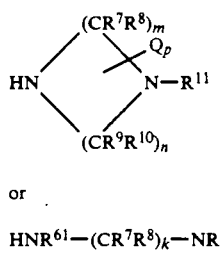

IX or $HNR^{61}$—$(CR^7R^8)_k$—$NR^{62}$—$Q_p$   X according to procedures in March, supra, pg. 445 to give the desired sulfonamide compound of formulas XIII and XIV. The sulfonamides XIII and XIV can be recovered by conventional recovery procedures such as distillation, filtration, solvent evaporation, crystallization, chromatography and the like.

Process B. In an alternative process, the compounds of formulas I and II can be contacted with about one equivalent amount (mole basis) of a sulfonating agent such as fuming sulfuric acid ($H_2SO_4$) or chlorosulfonic acid ($ClSO_3H$) as taught in March, supra, pp. 473–475 to give a sulfonated compound of formulas XI and XII:

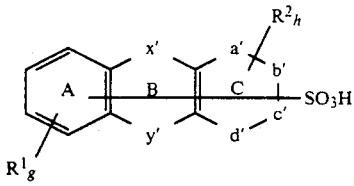

XI and

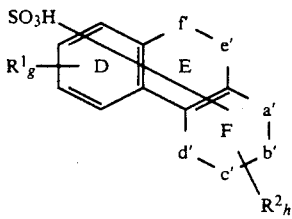

XII

The sulfonated compound of formulas XI and XII can then contacted with a chlorinating agent such as phosphorous pentachloride ($PCl_5$) as taught in March, supra pg. 445 to give the sulfonyl chloride of formulas VII and VIII. The sulfonyl chloride of formulas VII and VIII can be contacted with a diamine compound of formulas IX and X according to March supra, pg. 445 to give the desired compounds of formula XIII and XIV.

Process C. In a third alternative process, the sulfonyl chloride of formulas VII and VIII can be prepared directly by contacting the compounds of formulas I and II with excess chlorosulfonic acid ($ClSO_3H$) as described in March, supra pg. 475. The sulfonyl chloride of formulas VII and VIII thus prepared, can be further contacted with the diamine compounds of formulas IX and X as described in Processes A and B to give the desired sulfonamide compounds of formulas XIII and XIV.

PREPARATION OF STARTING MATERIALS a. Preparation of Aromatic Starting Materials. The tricyclic compounds of formulas I and II are known to those skilled in the art, as taught in R. C. Elderfield (ed.), Heterocyclic Compounds, Volumes 1–9, John Wiley & Sons, New York, N.Y., (1967), and G. P. Ellis, Synthesis of Fused Heterocycles, Volumes 1–47, John Wiley & Sons, New York, N.Y., (1987), whose preparative teachings are incorporated herein by reference.

b. Preparation of the Diamine Starting Materials. The diamine starting materials are known to those skilled in the art and can be prepared by conventional procedures. One such procedure is described in the Chem. Pharm Bulletin, Volume 29, pp. 684 (1981) and in the Journal Organic Chemistry, Volume 15, pg. 68 (1950). The reaction scheme for preparing the diamine compounds of formula can be set forth as follows:

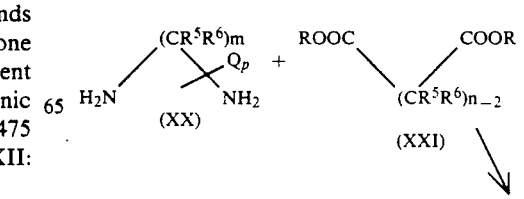

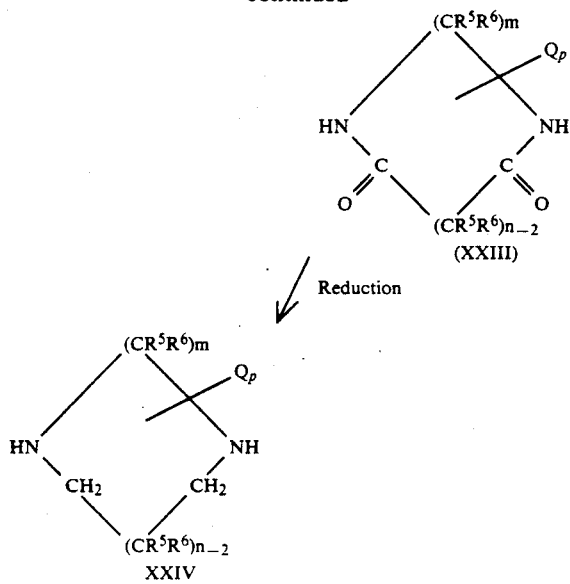

Essentially, a diamine compound of formula (XX) wherein $R^5$, $R^6$, Q, p and m are as defined hereinbefore, is contacted with a dicarboxylate compound of formula XXI wherein $R^5$ and $R^6$ are as defined hereinbefore and $n-2$ represents the same values for n less 2 for the two carboxylate carbons to give the cyclic diamide of formula (XXIII). Reduction of the cyclic diamide (XXIII) with a reducing agent such as lithium aluminum hydride (LAH) gives a cyclic diamine of formula (XXIV).

In a second procedure, the diamine compounds can be prepared according to the procedures of Tsizin. Khim, Volume 4, pg. 514, 1980, the Journal of the American Chemical Society, Volume 52, pp. 1202 (1940) and the Journal of Medicinal Chemistry, Vol. 15, pg 291 (1972). The procedure may be generally set forth as follows:

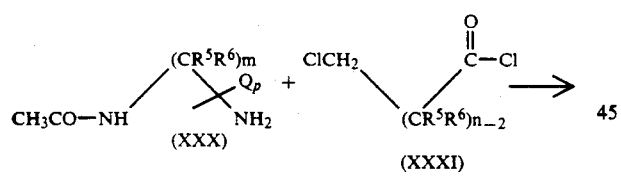

wherein $R^5$, $R^6$, Q, $k-2$ and m are as defined hereinbefore. The compound of formula (XXXII) may similarly reduced to a compound of formula (XXIV) with a reducing agent such as lithium aluminium hydride (LAH).

c. Preparation of the Acyclic Diamine Starting Materials. The acyclic diamine starting materials $NR^{61}—(CR^7R^8)_k—NR^{62}$ of formula (X) wherein k, $R^7$ and $R^8$ are as defined hereinbefore, and $R^{61}$ and $R^{62}$ independently represent hydrogen or alkyl, preferably hydrogen for purposes of substitution, are known as taught, for example, in Izvest. pg. 1488 (1969) (Chemical Abstracts: 54(1264) and in W. R. Sorenson and T. W. Campbell Preparative Methods of Polymer Chemistry, Interscience Publishers, New York, N.Y., pp 504 (1968).

Group Q as represented by $—L_q—T_r—R^{12}$ can be inserted on either the cyclic or acyclic starting materials by known methods. In the case where L represents —CO— the diamine starting material of formulas (XXIV) and (XXV) can be contacted with an acid chloride according to March. pp. 370–371 as follows:

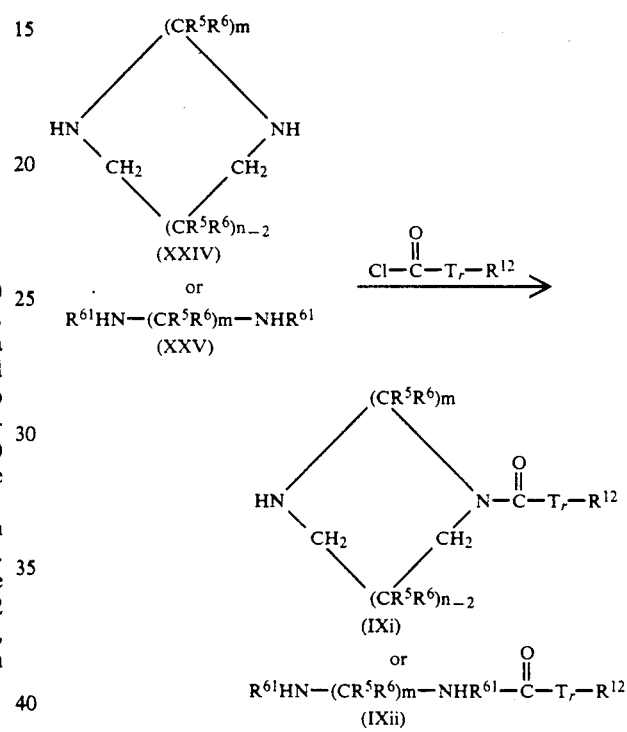

In the case where L represents —COO— the diamine starting material of formulas (XXIV) and (XXV) can be contacted with a chloroformate of formula (XXVI) according to March. pp. 370–371 as follows:

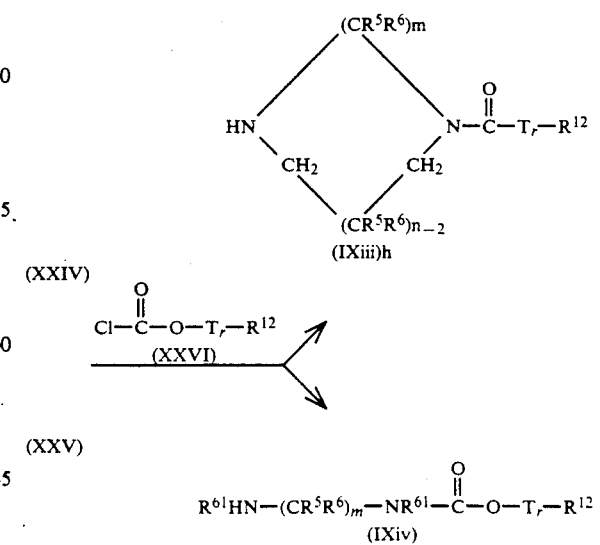

In the case where L represents —CONR$^{21}$R$^{22}$— the diamine compounds of formulas (IXiii) and (IXiv) wherein —T$_r$—R$^{12}$ represents alkyl, can be contacted with an appropriate amide as described in March pp 375 to give the corresponding substituted urea. Alternatively, the diamines of formulas (XXIV) and (XXV) can be contacted with the appropriate isocyanate, as described in March, pp. 802–803 to give the corresponding substituted urea.

In the case where L represents —SO$_2$NR$^{21}$— wherein R$^{21}$ is as defined hereinbefore, the diamine compounds of formulas (XXIV) and (XXV) can be contacted with the appropriate sulfonyl chloride, as described in March, supra, pg. 445 to give the corresponding sulfonamide.

In the case where Q represents the guanidine moiety —C(=NH)NR$^{31}$R$^{32}$ wherein R$^{31}$ and R$^{32}$ are as defined hereinbefore, the diamine compounds of formulas (XXIV) and (XXV) can be contacted with methylthiopseudo urea compound of formula

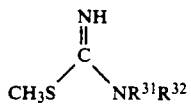
(XXVI)

wherein R$^{31}$ and R$^{32}$ are as defined hereinbefore, as taught in E. Brand, Organic Syntheses, Vol. 22, pg. 59 (1942), to give the corresponding guanidine. Other procedures for preparing the corresponding guanidine can be found in March, supra, pp. 359.

The following examples illustrate representative methods for preparing the compounds of the present invention, but as such, should not be construed as limitations upon the overall scope of the same.

EXAMPLE 1

1-(9-Anthracenylsulfonyl)hexahydro-1H-1,4-Diazepine hydrochloride

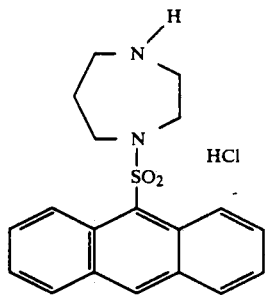

Step 1: Lithium 9-Anthracenesulfinate: Add a solution of n-Butyllithium in hexanes (9.38 milliliters (mL), 1.6 molar (M), 15 millimoles (mmol), 1.01 equivalents (eq)) to 9-bromoanthracene (3.82 g, 14.86 mmol) in anhydrous tetrahydrofuran (THF) (80 mL) cooled to −60 degrees Celsius (°C.) and protected by an argon atmosphere over 5 minutes (min). Warm the reaction mixture to 0° C. for 20 min then cool it back to −60° C. Add the reaction mixture to sulfur dioxide (40 mL) in anhydrous THF (80 mL) cooled to −60° C. dropwise with efficient stirring and protected from moisture with drierite®, trademark of W. A. Hammond, Drierite Co., Xenia, Ohio 45385, for a special form of anhydrous calcium sulfate having a highly porous granular surface and a high affinity for water. The reaction mixture is stirred at −60° C. for 30 min past addition, warmed to room temperature and stirred for 15 h allowing the excess sulfur dioxide to evaporate. The solvent is removed in vacuo and the resulting solid triturated twice with n-hexane (50 mL) to give the sulfinate salt as a light brown solid (3.05 g, 83 percent (%), Rf=0.46 (15% MeOH/CH$_2$Cl$_2$ (volume/volume basis(v/v)), 0.2% HOAc buffer).

Step 2: 9-Anthracenesulfonyl chloride: Sulfuryl chloride (0.21 g, 2.62 mmol) dissolved in n-hexane (7 mL) is added dropwise over 3 min to the product of step 1 (0.65 g) suspended in n-hexane (15 mL), cooled to °C. and protected from moisture. The reaction mixture is stirred at 0° C. for 5 min, warmed to room temperature and filtered. Suspend the solid in methylene chloride (50 mL) for 1 min, filter, and remove the solvent in vacuo to give the sulfonyl chloride compound (0.35 g) as a light yellow solid. Rf=0.44 (5% ethyl acetate in hexanes (v/v)).

Step 3: Add the product from step 2 (0.35 g, 1.28 mmol) in methylene chloride (20 mL) to a mixture of triethyl amine (0.605 mL, 4.34 mmol) and hexahydro-2H-1,4-diazepine (also known as homopiperazine) (0.326 g, 3.25 mmol) in methylene chloride (7 mL) cooled to 0° C. over 5 min. Stir the reaction mixture for 15 min at 0° C. Add aqueous HCl (25 mL, 1N) to the reaction mixture. Filter the solid and recrystallize from absolute ethanol to give the title compound (0.33 g, 69%) as light yellow needles. Rf=0.54 (5% MeOH in methylene chloride (v/v), 0.2% ammonium hydroxide buffer).

EXAMPLE 2

1-((9-bromo-2-phenanthrenyl)sulfonyl)hexahydro-1H-1,4-diazepine, hydrochloride

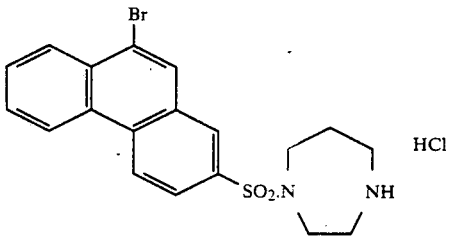

Step 1: 9-Bromo-2-phenanthrenene sulfonic acid: Add 9-bromophenanthene (2 g, 7.8 mmol) in portions over 3 min to concentrated sulfuric acid (0.43 mL, 7.8 mmol) heated to 100° C. Continue heating for 18 h with efficient stirring. Cool the reaction mixture to room temperature. Partition the reaction mixture between ethyl acetate (75 mL) and aqueous hydrochloric acid (50 mL, 1N). Extract the separated aqueous twice with ethyl acetate (50 mL), and combine. Concentrate in vacuo to give a mixture of sulfonic acids (2.42 g) as a brown waxy solid. Rf=0.35 (15% methanol in methylene chloride (v/v), 0.2% acetic acid buffer).

Step 2: 9-Bromo-2-phenanthrene sulfonyl chloride: Add the product of step 1 (2.42 g, 7.2 mmol) to phosphorus oxychloride (30 mL) and phosphorus pentachloride (2.24 g, 1.5 eq). Reflux the reaction mixture for 5 hours. Cool the reaction mixture to 0° C. Add cautiously to crushed ice (1 L) with stirring. Extract the aqueous suspension with methylene chloride (400 mL). Wash the methylene chloride solution with saturated aqueous sodium bicarbonate (200 mL), saturated sodium chloride (200 mL). Dry the methylene chloride layer (MgSO4), filter and concentrate in vacuo to give the sulfonyl chloride (2.35 g) as a yellow waxy solid mixture of isomers. Rf=0.56 (5% ethyl acetate:hexanes).

Step 3: Add the product of step 2 (2.35 g) in methylene chloride (70 mL) dropwise to hexahydro-2H-1,4-diazepine (0.66 g, 6.6 mmol), triethylamine (1.38 mL, 9.9 mmol) in methylene chloride (35 mL) cooled to 0° C. over 10 minutes. Warm the reaction to room temperature for 30 minutes. Concentrate in vacuo to a yellow solid. Chromatograph the solid on a column of silica gel (500 g) eluting with 4:1:95 methanol:ammonium hydroxide:methylene chloride (2 L) to give the title compound, a free base (1.75 g) as a 6.5:1 mixture of isomers. Rf=0.52 5:95 methanol:methylene chloride containing 0.2% ammonium hydroxide). Dissolve the mixture of isomers in aqueous hydrochloric acid (5 mL, 1N) and concentrate to a white solid. Separate the isomers (100 mg) on a high pressure reversed-phase silica gel column (C18 Dynamax Semiprep 60A ®, trademark of Rainin Instruments, Woburn, Mass. 01801) eluting with a 35:65 mixture of water:methanol buffered with 0.2% trifluoroacetic acid at a flow rate of 10 mL/minute to give 65 mg of the title compound.

EXAMPLE 3

1-(1-Anthracenylsulfonyl)hexahydro-1H-1,4-diazepine hydrochloride and
1-(2-Anthracenylsulfonyl)hexahydro-1H-1,4-diazepine hydrochloride

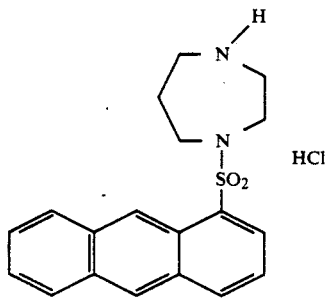

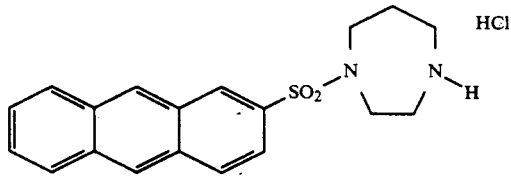

Step 1: 1(or 2)-anthracenesulfonic acid: Add fuming sulfuric acid (20%, 12 mL) dissolved in glacial acetic acid (25 mL) dropwise to a stirred suspension of anthracene (10 g, 56 mmol) in glacial acetic acid (100 mL) cooled to 10° C. at a rate sufficient to prevent warming. Stir the reaction mixture at 10° C. for 10 minutes. Heat the reaction mixture to 70° C. for 4 hours. Cool to room temperature, filter unreacted anthracene, and concentrate in vacuo to an oil. Partition the oil between ethyl acetate (200 mL) and water (200 mL). Extract the water layer twice with ethyl acetate (150 mL) and combine with the first ethyl acetate extract and concentrate in vacuo. Dissolve in n-heptane (100 mL) and concentrate in vacuo removing azeotropically the last traces of acetic acid to give the sulfonic acid (9.7 g, 76%) as a 2:1 mixture of the 1- and 2-anthracene sulfonic acids as a light brown solid. Rf=0.44 (15:85 methanol:methylene chloride, 0.2% acetic acid buffer. HPLC 1-isomer 8.3 minutes, 2-isomer 10.3 minutes retention time (1:1 methanol:water, 0.2% trifluoroacetic acid buffer, C18 reversed-phase silica analytical (Waters Associates, Inc. Massachusetts), 1.0 mL/minute flow rate).

Step 2: 1(or 2)-anthracenesulfonyl chloride: Add phosphorus pentachloride (11.73 g) in portions over 3 minutes to a suspension of the product of step 1 (9.7 g, 38 mmol) in phosphorus oxychloride (75 mL). Heat the reaction mixture to reflux for 4 hours. Cool to 0° C. and add cautiously to crushed ice (1.5 L). Extract with methylene chloride (500 mL). Wash the organic layer with saturated aqueous sodium bicarbonate (500 mL). Dry (MgSO4) and decolorizing carbon (1 g), filter and concentrate in vacuo to give the sulfonyl chloride (9.9 g) as a mixture of the 1- and 2-isomers as a yellow solid. Rf=0.36 5:95 ethyl acetate:hexanes.

Step 3: Add the product of step 2 (9.9 g) in methylene chloride (100 mL) dropwise over 20 minutes to hexahydro-2H-1,4-diazepine (5.37 g) and triethylamine (9.96 mL) in methylene chloride (50 mL) cooled to 0° C. Stir for 30 minutes, wash with hydrochloric acid (50 mL, 1N), then saturated aqueous sodium chloride (100 mL). Dry (MgSO4), filter and concentrate to give a yellow solid (10.1 g). Chromatograph the solid on a column of silica gel (200 g, 60 micron particle size) eluting with 4:1:95 methanol:ammonium hydroxide:methylene chloride to give the title compound, a free base (6.4 g) as a yellow foam. Dissolve in hydrochloric acid and concentrate to give the title compounds as a mixture of yellow solids. Separate the isomers by chromatography on a reversed-phase C18 high performance silica column (Rainin Instruments, supra) eluting with 35:65 acetonitrile:water buffered with 0.2% trifluoroacetic acid at an elution rate of 10 ml/min. Rf=0.62 (minor), 0.55 (major) of free-base mixture (5:95 methanol:methylene chloride, 0.2% ammonium hydroxide buffer).

EXAMPLE 4

1-((7-bromo-9H-fluoren-2-yl)sulfonyl)hexahydro-1H-1,4-diazepine, hydrochloride

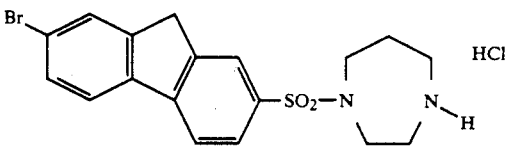

Step 1: 7-Bromo-9H-fluorene-2-sulfonyl chloride: Add chlorosulfonic acid (1.33 mL, 20 mmol) to 2-bromofluorene (2.45 g, 10 mmol) in methlene chloride (50 mL) dropwise over 20 minutes. Stir 18 hours at room temperature. Concentrate in vacuo to a solid. Suspend in phosphorus oxychloride (25 mL) and add phosphorus pentachloride (2 g) in portions over 10 minutes. Heat the reaction mixture to reflux for 3 hours. Cool the reaction mixture to room temperature and pour the contents cautiously onto crushed ice (200 mL). Extract the mixture with methylene chloride (100 mL). Wash the organic layer with saturated aqueous sodium bicarbonate (50 mL), then saturated aqueous sodium chloride (50 ml). Dry the organic layer (MgSO4), filter, and concentrate in vacuo to an orange solid. Recrystallize from hexane:ethyl acetate 95:5 to give the sulfonyl chloride (2.57 g) as a light yellow crystalline solid. Rf=0.59 (100% ethyl acetate). Calculated for C13H6O2SClBr: C, 45.72; H, 1.77; S, 9.37; Cl, 10.38; Br 23.39. Observed: C, 46.50; H, 2.26; S, 9.45; Cl, 10.55; Br, 23.85.

Step 2: Add the product of step 1 (1.0 g, 2.9 mmol) in methylene chloride (10 mL) dropwise over 10 minutes to hexahydro-2H-1,4-diazepine (0.35 g) in methylene chloride (20 mL). Stir for 18 hours. Partition the reaction mixture between ethyl acetate (75 mL) and hydrochloric acid (75 mL, 1N). Separate, and adjust the pH of the aqueous layer to alkaline pH (phenolphthalein indicator) with aqueous sodium hydroxide (1N) forming a heavy precipitate. Extract the reaction mixture with methylene chloride (100 mL), wash with saturated aqueous sodium bicarbonate (100 mL), saturated aqueous sodium chloride (100 mL). Dry (MgSO4), filter and concentrate in vacuo to give the title compound free base (0.87 g) as a light yellow solid. Rf=0.52 (450:45:5 methylene chloride:methanol:acetic acid). Chromatograph the free base (120 mg) on a column of silica gel (300 g, 60 micron particle size) eluting with 1:9 methanol:methylene chloride to give a solid. Dissolve the solid in hydrochloric acid (10 mL) and concentrate to give the title compound (110 mg) as a white solid, as the semihydrate. Calculated for C18H21O2.5N2SBrCl: C, 47.76; H, 4.68; N, 6.18. Observed: C, 47.76; H, 4.39; N, 6.14.

EXAMPLE 5

1-((7-bromo-9,9-dimethyl-9H-fluoren-2-yl)sulfonyl)hexahydro-1H-1,4-diazepine hydrochloride

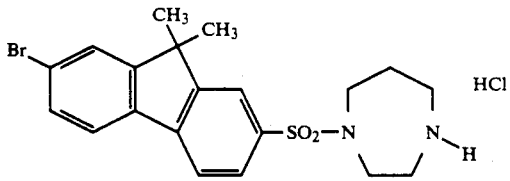

Step 1: 2-Bromo-9,9-dimethylfluorene: Add potassium bis(trimethylsilyl)amide (45 mL, 0.5M in toluene, 1 eq.) dropwise over 5 minutes to 2-bromofluorene (5 g, 20.4 mmol) in anhydrous THF (20 mL) cooled to 0° C. and protected by a nitrogen atmosphere. The reaction color becomes a deep red. Stir the reaction for 10 minutes at 0° C. Add methyl iodide (1.4 mL) in one portion. Stir the reaction mixture during which the red color discharges. Add potassium bis(trimethylsilyl)amide (45 mL, 0.5M in toluene, 1 eq.) dropwise over 5 minutes. The reaction color again becomes a deep red. Stir 10 minutes at 0° C. Add methyl iodide (1.4 mL). Stir the reaction mixture for 30 minutes during which the red color discharges. A heavy precipitate forms. Warm the reaction mixture to room temperature. Partition the reaction mixture without filtration between ethyl acetate (200 mL) and aqueous hydrochloric acid (300 mL, 0.1N). Wash the organic layer with aqueous saturated sodium bicarbonate (200 mL). Dry and decolorize the organic layer (MgSO4) and decolorizing carbon (1 g), filter and concentrate in vacuo to give the alkylated fluorene (5.64 g) as a viscous yellow oil. Rf=0.85 (20:80 ethyl acetate:hexanes), Calculated for C15H12O2SClBr: C, 65.95; H 4.80; Br, 29.25. Observed: C, 64.83; H, 4.88; Br, 27.99.

Step 2: 7-Bromo-9,9-dimethylfluorene-2-sulfonyl chloride: Add chlorosulfonic acid (0.7 mL, 10.1 mmol) in methylene chloride (5 mL) dropwise over 10 minutes to the product of step 1 (2.5 g, 9.2 mmol, 1 eq) dissolved in methylene chloride (50 mL). Stir the reaction mixture protected from moisture for 18 hours. Concentrate in vacuo and dissolve in phosphorus oxychloride (50 mL). Add phosphorus pentachloride (5 g) in portions with brisk stirring. Heat the reaction mixture to reflux for 2.5 hours. Cool the reaction mixture to room temperature and add cautiously to crushed ice (400 mL), dilute with water (300 mL) and extract twice with methylene chloride (200 mL). Wash the organic layer with saturated aqueous sodium bicarbonate (300 mL), saturated aqueous sodium chloride (300 mL). Dry the organic layer (MgSO4), filter and concentrate in vacuo to give an oil (3.54 g) which solidifies. Recrystallize the solid from 1:1 ethyl acetate:hexane to give the sulfonyl chloride (2.09 g, 61%) as a light yellow solid. Rf=0.66 (20:80 ethyl acetate:hexanes), Rf=0.10 (100% hexanes). Calculated for C15H12O2SClBr: C, 48.48; H, 3.26; S, 8.61; Cl, 9.54; Br, 21.50. Observed: C, 45.17; H, 3.44; S, 9.00; Cl, 7.88; Br, 18.76.

Step 3: Add the product of step 2 (0.5 g, 1.3 mmol) as a suspension in methylene chloride (10 mL) to hexahydro-2H-1,4-diazepine erazine (0.16 g) in methylene chloride (5 mL) at room temperature over 5 minutes. Stir the reaction mixture for 18 hours. Add aqueous sodium hydroxide (50 mL, 0.1N) to the reaction mixture, separate, and dry the organic layer (MgSO4), filter and concentrate to the title compound free base as a white solid. Chromatograph the solid on a column of silica gel (300 g) eluting with 5:95 methanol:methylene chloride. The solid is dissolved in aqueous hydrochloric acid (50 mL, 1N), concentrated, redissolved in water (25 mL) and lyophilized to give the title compound hydrate (200 mg, 31%) as a white solid. Rf=0.30 (1:9 methanol:methylene chloride). Calculated for C20H26O3N2SCl2Br: C, 49.04; H, 5.35; N, 5.72; S, 6.53. Observed: C, 48.62; H, 4.64; N, 5.70; S, 6.52.

EXAMPLE 6

4-((7-bromo-9H-fluoren-2-yl)sulfonyl)hexahydro-1H-1,4-diazepine-1-carboxaldehyde

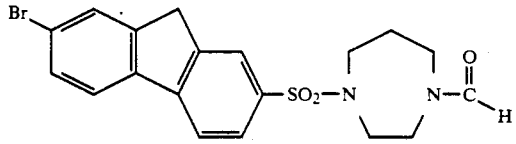

Add the product of example 4, step 3 free base (0.5 g) to ethyl formate (100 mL) and reflux for 3 days. Cool the reaction mixture and remove the solvent in vacuo to give the title compound (0.55 g) as a light tan solid. Rf=0.33 (100% ethyl acetate). Rf=0.79 (1:9 methanol:methylene chloride). Calculated for C19H19O3N2SBr: C, 52.42; H, 4.40; N, 6.43. Observed: C, 52.45; H, 4.51; N, 6.51.

EXAMPLE 7

1-((7-bromo-9H-fluoren-2-yl)sulfonyl)hexahydro-4-methyl-1H-1,4-diazepine hydrochloride

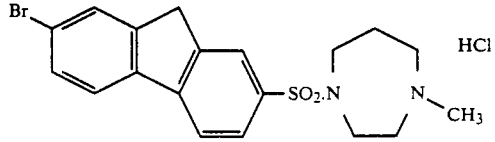

Add the product of Example 6 (0.52 g, 1.2 mmol) as a slurry in anhydrous tetrahydrofuran (10 mL) to borane-tetrahydrofuran complex (2 mL, 1N in tetrahydrofuran), over 2 minutes at 0° C. and protect with a nitrogen atmosphere. Heat the reaction mixture to reflux for 30 minutes. Cool the reaction mixture back to room temperature, add borane-tetrahydrofuran complex (2 mL). Heat to reflux for 1 hour. Cool the reaction mixture back to room temperature. Add aqueous hydrochloric acid (20 mL, 1N) cautiously, then partition between water (50 mL) and methylene chloride (50 mL). Adjust the pH of the aqueous layer to greater than 12 with aqueous sodium hydroxide, and extract twice with methylene chloride (50 mL). Wash the methylene chloride extract with saturated aqueous sodium chloride (50 mL), dry (MgSO4), filter and concentrate to a solid. Chromatograph the solid on a column of silica gel (300 g, 60 micron particle size) eluting with 5:95 methanol:-methylene chloride with a flow rate of 10 mL/minute to give a yellow solid. Dissolve the solid in hydrochloric acid (50 mL, 1N), and concentrate in vacuo to give the title compound bis hydrate (120 mg) as a light yellow crystalline solid. Free base Rf=0.44 (1:9 methanol:-methylene chloride). Calculated for C19H26O4N2SClBr: C, 46.21; H, 5.30; N, 5.67. Observed: C, 45.61; H, 4.52; N, 5.63.

EXAMPLE 8

4-((7-bromo-9H-fluoren-2-yl)sulfonyl)hexahydro-1,1-dimethyl-1H-1,4-diazepinium iodide

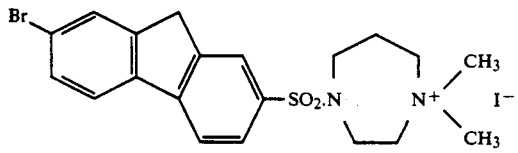

Add methyl iodide (0.35 g, 2.5 eq) in one portion to the free base product of Example 4, Part 3 (0.25 g, 0.6 mmol) in methylene chloride (10 mL) and potassium carbonate (0.25 g) at room temperature and protected from moisture. Stir for 3 days. Filter and concentrate to a solid. Chromatograph the solid on a column of reversed phase silica gel (300 g, C18, 60 micron particle size) and elute with mixtures of water:methanol (linear gradient from 100% water to 100% methanol over 2 hours, 0.2% trifluoroacetic acid buffer) to give a solid. Add the solid to hydrochloric acid (10 mL, 1N) and concentrate to give the title compound (100 mg) as a mixed salt (1:1 iodide:trifluoroacetate). Rf=0.22 (product), 0.76 (mono-N-alkylated intermediate) (450:45:5 methylene chloride:methanol:acetic acid). Calculated for C21H24O3N2SBrF1.510.5: C, 45.33; H, 4.34; N, 5.03. Observed: C, 44.77; H, 3.98; N, 4.68.

EXAMPLE 9

1-((7-Bromo-9H-fluoren-2-yl)sulfonyl)-3,5-dimethylpiperazine hydrochloride

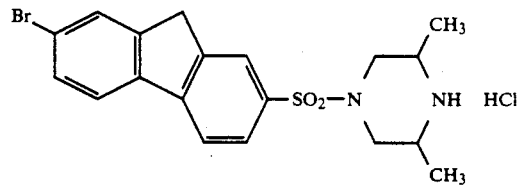

Add the product of Example 4, Step 2 (0.5 g, 1.5 mmol) in methylene chloride (10 mL) to 2,5-dimethylpiperazine (0.2 g, 1.1 eq) and triethylamine (2 mL) in methylene chloride (10 mL) at room temperature over 5 minutes. Stir the reaction mixture 18 hours. Filter and concentrate to a gum. Chromatograph the gum on a column of silica (300 g) eluting with 1:9 methanol:-methylene chloride (4 L) to give the free base as a solid. Dissolve the solid in hydrochloric acid (10 mL, 1N), and concentrate in vacuo to give the title compound monohydrate (0.42 g, 75%) as a light yellow solid. Rf=0.41 (free base) (1:9 methanol:methylene chloride). Calculated for C19H24O3N2SBrCl: C, 47.97; H, 5.08; N, 5.89; S, 6.73; Cl, 7.45; Br, 16.79. Observed: C, 48.03; H, 5.01; N, 5.61; S, 6.74; Cl, 8.40; Br, 15.27.

EXAMPLE 10

1-(2-Phenanthridinylsulfonyl)-hexahydro-1H-1,4-diazepine dihydrochloride,
1-(7-Phenanthridinsulfonyl)-hexahydro-1H-1,4-diazepine dihydrochloride and
1-(8-Phenanthridinsulfonyl)-hexahydro-1H-1,4-diazepine dihydrochloride

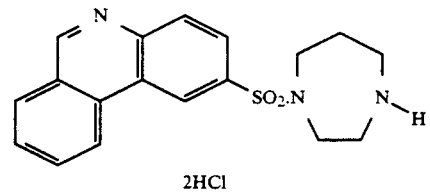

2HCl

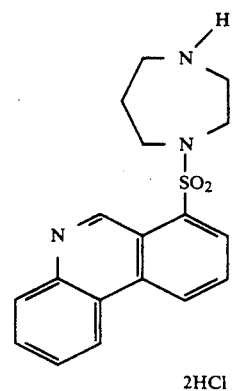

2HCl

-continued

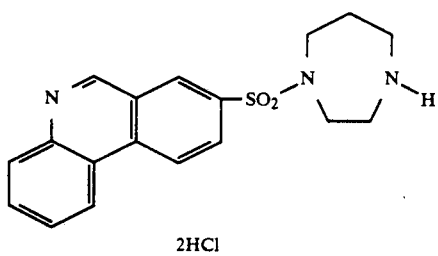

2HCl

Step 1: Phenanthridinesulfonic acid: Add phenanthridine (5 g, 28 mmol) in portions to chlorosulfonic acid (5.6 mL, 84 mmol) cooled to 10° C. over 20 minutes Heat the reaction mixture to reflux for 20 hours. Cool the now black reaction mixture to 0° C. and add cautiously to crushed ice (500 mL). Filter the solid and dry in vacuo to give the sulfonic acid (3.61 g) as an ivory colored solid consisting of a partially resolved 7:3 mixture of regioisomers. Rf=0.35 (major), 0.19 (minor (15:85 methanol:methylene chloride, 0.2% acetic acid buffer).

Step 2: Phenanthridinesulfonyl chloride: Add phosphorus pentachloride (2.4 g, 1.5 eq., 11.5 mmol) to the product of step 1 (2 g, 7.7 mmol) suspended in phosphorus oxychloride (30 mL) in portions over 5 minutes. Heat the reaction mixture to reflux for 5 hours. Cool to 0° C. and add cautiously to crushed ice (1 L). Extract with methylene chloride (200 mL). Wash the organic layer with aqueous saturated sodium bicarbonate (200 mL), aqueous saturated sodium chloride (200 mL). Dry the organic layer (MgSO4), filter and concentrate in vacuo to give a yellow solid (1.84 g). Rf=0.94 (major), 0.61, 0.51 (minors) (1:99 methanol:methylene chloride).

Step 3: Add the product of step 2 (1.84 g) in methylene chloride (70 mL) dropwise to hexahydro-2H-1,4-diazepine (0.99 g) and triethylamine (1.85 mL) in methylene chloride (35 mL) cooled to 0° C. over 15 minutes. Warm the reaction mixture to room temperature and stir 1 hour. Extract the methylene chloride solution with hydrochloric acid (50 mL, 1N), separate and concentrate the aqueous layer to a solid. Dissolve the solid in methanol:water 1:1 (100 mL) and adjust the pH to 12 with ammonium hydroxide. Extract the aqueous with ethyl acetate (100 mL) and concentrate to give the free base (1.8 g) as a white foam. Dissolve the foam in hydrochloric acid (20 mL, 1N) and concentrate to give the product as a mixture of isomers (2 g) as the hydrochloride salt. Chromatograph the mixture (200 mg) on a reversed-phase C18 silica column (200 g, 20 micron) eluting with methanol:water 1:1, 0.2% trifluoroacetic acid buffer (10 mL/minute flow rate) separating the isomers to give minor 1 (45 mg), minor 2 (27 mg), and the title compound (97 mg) as yellow solids. HPLC retention times were 5.76, 7.11, and 8.06 minutes for minor 1, minor 2, and the title compound at a 1 mL flow rate, respectively (analytical reversed-phase C18 silica column, Waters Assoc., supra.).

EXAMPLE 11

1-(1-Acridinylsulfonyl)-1H-1,4-diazepine dihydrochloride, hemihydrate

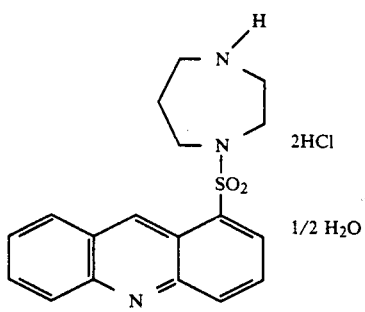

2HCl

1/2 H2O

Step 1: 1-Acridinesulfonyl chloride: Add acridine (5 g, 28 mmol) in portions to chlorosulfonic acid (7 mL, 2.2 eq) over 5 minutes with efficient stirring. Heat the reaction mixture to reflux for 5 hours. Cool the reaction mixture to room temperature and add cautiously to crushed ice (200 mL). Adjust the suspension to alkaline pH (phenolphthalein indicator) with sodium bicarbonate solid added in portions. Extract with methylene chloride (100 mL), wash the organic layer with saturated aqueous sodium carbonate (100 mL), saturated aqueous sodium chloride (100 mL). Dry the organic layer (MgSO4), filter and concentrate in vacuo to give an orange solid. Chromatograph on a column of silica gel (800 mL) eluting with 3:2 ethyl acetate:hexane to give the sulfonyl chloride as an apparent mixture of isomers (2.71 g) and the acridine-1,8-disulfonyl chloride (2.28 g) side product, both as yellow solids. Rf=0.85 (mono), 0.50 (di) (100% ethyl acetate)

(mono) calculated C13H8O2NSCl: C, 56.24; H, 2.90; N, 5.04; S, 11.53; Cl, 12.77. Observed: C, 50.04; H, 2.60; N, 4.35; S, 13.36; Cl, 14.31.

(di) calculated C13H7O4NS2Cl2: C, 41.52; H, 1.88; N, 3.72; S, 17.02; Cl, 18.85. Observed: C, 41.64; H, 1.83; N, 3.61; S, 16.74; Cl, 18.75.

Step 2: Add the product of step 1 (1 g) in methylene chloride (20 mL) to hexahydro-2H-1,4-diazepine (0.54 g, 1.5 eq) and triethylamine (1 mL, 2.0 eq) in methylene chloride (25 mL) dropwise over 10 minutes. Stir for 18 hours. Add hexahydro-2H-1,4-diazepine (0.54 g, 1.5 eq additional) and stir 18 hours. Extract the reaction mixture with hydrochloric acid (100 mL, 1N), adjust the pH of the aqueous to alkaline pH (phenolphthalein indicator) with aqueous sodium hydroxide (1N) to give a white precipitate. Extract twice with methylene chloride (200 mL), combine, dry (MgSO4), filter, and concentrate to give a white solid. Chromatograph the solid on a column of silica gel (300 g) eluting with 1:9 methanol:methylene chloride, 0.5% ammonium hydroxide buffer (2 L) then 15:85 methanol:methylene chloride 0.5% ammonium hydroxide buffer (2 L) to give the title compound free base as a white solid. Dissolve the solid in anhydrous ethanol saturated with hydrogen chloride gas (25 mL), and concentrate in vacuo to give the title compound (250 mg), a white solid, 0.5 equivalent hydrate. Calculated for C18H21O2.5N3SCl: C, 51.08; H, 5.24; N, 9.92; S, 7.56; Cl, 16.75. Observed: C, 51.04; H, 5.31; N, 9.36; S, 7.79; Cl, 14.33.

EXAMPLE 12

1-((10,11-dihydro-5H-dibenzo(a,d)cycloheptene-2 or -3-yl)sulfonyl)hexahydro-1H-1,4-diazepine hydrochloride, disodium chloride

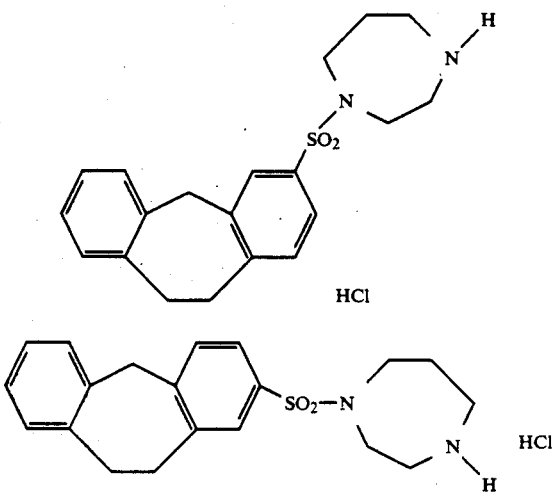

Step 1: 2-(or 3)-(10,11-dihydro-5H-dibenzo(a,d)cycloheptene)-sulfonyl chloride: Add chlorosulfonic acid (0.75 mL, 1.1 eq) in methylene chloride (10 mL) dropwise over a 10 minute period to 10,11-dihydro-5H-dibenzo(a,d)cycloheptene-2 (2.0 g, 10.3 mmol, 1 eq) in methlene chloride (20 mL) at 0° C. Stir at 0° C. for 1 hour, add chlorosulfonic acid (0.2 mL) and stir 1 hour at 0° C. Warm the reaction to room temperature and remove the solvent in vacuo to give an oil. Dissolve the oil in phosphorus oxychloride (25 mL) and add phosphorus pentachloride (3 g) cautiously. Heat the reaction mixture to reflux for 3 hours. Cool to room temperature and add cautiously to crushed ice (300 mL). Extract with methylene chloride (200 mL), wash the organic layer with saturated aqueous sodium bicarbonate (200 mL), saturated aqueous sodium chloride (200 mL). Dry the organic (MgSO4), filter and concentrate to an oil. Chromatograph the oil on a column of silica gel (300 g, 60 micron particle size) eluting with 1:9 ethyl acetate:hexanes to give the sulfonyl chloride (1.7 g) as a yellow solid, a 1:1 mixture of the 2- and 3-isomers. Rf=0.51 and 0.46 (1:9 ethyl acetate:hexanes). Calculated C15H13O2SCl: C, 61.55; H, 4.48; S, 10.93; Cl, 12.11. Observed: C, 60.80; H, 4.44; S, 10.41; Cl, 11.58.

Step 2: The product of step 1 (0.5 g) in methylene chloride (10 mL) is added dropwise to hexahydro-2H-1,4-diazepine (0.2 g) and triethylamine (2 mL) in methylene chloride (10 mL) over 3 minutes. The reaction mixture is stirred for 4 hours, filtered, and concentrated to an oil. Chromatograph the oil on a column of silica gel (300 g, 60 micron particle size) eluting with 5:95 methanol:methylene chloride to give the title compound, a free base, as a solid. The solid is dissolved in hydrochloric acid (25 mL, 1N) and concentrated in vacuo to give the title compound (0.48 g, 72%) as a light yellow solid. Calculated for C20H24O2N2S.HCl.(0.2 NaCl): C, 59.38; H, 6.22; N, 6.92; S, 7.91; Cl, 10.51. Observed: C, 59.14; H, 6.24; N, 6.73; S, 7.99; Cl, 8.85.

The compounds of the present invention are useful as antihypertensive agents, by reducing blood pressure in mammals in which the blood pressure has become abnormally elevated. Evidence of their antihypertensive properties is provided by their ability to inhibit the enzyme myosin light chain kinase (MLCK). Activation of MLCK is known to initiate smooth muscle contraction. Therefore, inhibiting MLCK will prevent smooth muscle contraction, resulting in vasodilation, as indicated by a decrease in blood pressure, as taught in K. E. Kamm. and J. T. Stull, Annu. Rev. Pharmacol. Toxicol. 25, 593–620, (1985).

The present compounds can be combined with a suitable pharmaceutical carrier to prepare a pharmaceutical preparation or composition suitable for parenteral or oral administration. Such pharmaceutical compositions are useful in the treatment of cardiovascular disorders such as mammalian hypertension.

The effective daily antihypertensive dose (ED$_{50}$) of the present compounds will typically be in the range of about 10 to about 100 mg/kg of mammalian body weight, administered in single or divided doses. The exact dosage to be administered can be determined by the attending clinician and is dependent upon where the particular compound lies within the above cited range, as well as upon the age, weight and condition of the individual.

Generally, in treating humans in need of treatment for hypertension, the present compounds can be administered in a dosage range of about 10 to about 500 mg per patient generally given a number of times per day, providing a total daily dosage of from about 10 to about 2000 mg per day.

The compositions of the present invention can be administered orally or parenterally. Typical injectable formulations include solutions and suspensions. Typical oral formulations include tablets, capsules syrups, suspensions and elixirs. Also contemplated are mechanical delivery systems, e.g. transdermal dosage forms.

The typical acceptable pharmaceutical carriers for use in the formulations described above are exemplified by sugars such as lactose, sucrose, mannitol and sorbitol; starches such as cornstarch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinylpyrrolidone, polyvinyl alcohol; stearic acid; alkaline earth metal stearates such as magnesium stearate and calcium stearate, stearic acid, vegetable oils such as peanut oil, cottonseed oil, sesame oil, olive oil and corn oil; non-ionic, cationic and anionic surfactants; ethylene glycol polymers; betacyclodextrin; fatty alcohols and hydrolyzed cereal solids; as well as other non-toxic compatible fillers, binders, disintegrants, buffers, preservatives, antioxidants, lubricants, flavoring agents, and the like commonly used in pharmaceutical formulations.

Following are typical examples of oral and parenteral formulations, wherein the term "Active Ingredient" refers to a compound of formula XIII or XIV.

EXAMPLE 13

A capsule comprising an Active Ingredient: e.g. 1-((7-bromo-9,9-dimethyl-9H-fluoren-2-yl)sulfonyl)hexahydro-1H-1,4-diazepine hydrochloride, 4-((7-bromo-9H-fluoren-2-yl)sulfonyl)hexahydro-1H-1,4-diazepine-1-carboxaldehyde, 1-((7-bromo-9H-fluoren-2-yl)sulfonyl)hexahydro-4-methyl-1H-1,4-diazepine hydrochloride, 4-((7-bromo-9H-fluoren-2-yl)sulfonyl)hexahydro-1,1-dimethyl-1H-1,4-diazepinium iodide or 1-((7-

Bromo-9H-fluoren-2-yl)sulfonyl)-3,5-dimethylpiperazine hydrochloride, is prepared from the following ingredients:

| Capsule | Amount (mg) | |
| --- | --- | --- |
| Active Ingredient | 250.0 | 125.0 |
| Lactose | 173.0 | 86.5 |
| Corn Starch | 75.0 | 37.5 |
| Magnesium Stearate | 2.0 | 1.0 |
| TOTAL | 500.0 | 250.0 |

Blend the active ingredient, lactose and corn starch until uniform; then blend the magnesium stearate into the resulting powder. Encapsulate the mixture into suitably sized two-piece hard gelatin capsules.

EXAMPLE 14

| Capsule | Amount (mg) | |
| --- | --- | --- |
| Active Ingredient | 250.0 | 125.0 |
| Lactose | 161.0 | 80.5 |
| Corn Starch | 12.0 | 6.0 |
| Water (per thousand tablets) | 120 ml (evaporates) (evaporates) | 60 ml |
| Corn Starch | 75.0 | 37.5 |
| Magnesium Stearate | 2.0 | 1.0 |
| TOTAL | 500.0 | 250.0 |

Blend the active ingredient with the lactose until uniform. Blend the smaller quantity of corn starch with the water and add the resulting corn starch paste then mix until a uniform wet mass is formed. Add the remaining corn starch to the remaining wet mass and mix until uniform granules are obtained. Screen the granules through a suitable milling machine, using a ¾ inch stainless steel screen. Dry the milled granules in a suitable drying oven until the desired moisture content is obtained. Mill the dried granules through a suitable milling machine using a 16 mesh stainless steel screen. Blend in the magnesium stearate and compress the resulting mixture into tablets of desired shape, thickness, hardness and disintegration.

EXAMPLE 15

| Injectable Solution | mg/ml |
| --- | --- |
| Active Ingredient | 5.00 |
| Methyl p-hydroxybenzoate | 0.80 |
| Propyl p-hydroxybenzoate | 0.10 |
| Disodium Edetate | 0.10 |
| Citric Acid Monohydrate | 0.08 |
| Dextrose | 40.0 |
| Water for injection qs. ad. | 1.0 ml |

Dissolve the p-hydroxybenzoates in a portion of water for injection at a temperature of between 60° C.–70° C. and cool the solution to 20° C.–30° C., Charge and dissolve all other excipients and the active ingredient. Bring the solution to final volume, filter it through a sterilizing membrane and fill into sterile containers.

Calcium-Calmodulin Independent Myosin Light Chain Kinase (MLCK) Assay

The MLCK assay is an in-vitro assay used to identify myosin light chain kinase inhibitors that do not antagonize calmodulin interactions with MLCK.

A. Enzyme Preparation. Calmodulin-independent myosin light chain kinase(CIM) of greater than 95 percent homogeneity is prepared by trypsin digestion of calmodulin-dependent MLCK which is prepared from chicken gizzard by the method of Ngai, P. J., Carruthers, C. A. and Walsh, M. P. (1984), Biochem. J. 218, pages 863–870, through the step employing diethylaminoethyl(DEAE)-Sephacel ®, trademark of Pharmacia Fine Chemicals, Inc., New Market, N.J. 08854. The kinase solution containing 8.5 mg protein is adjusted to 0.5 mg/ml in 20 mM Tris/HCl, pH 7.5, 2 mM EGTA. An aliquot of 1 mg/ml of N-tosyl-L-phenylalanine-chloromethyl ketone (TPCK) treated trypsin is added to a final trypsin:MLCK ratio of 1:7.5 (mg/mg protein). Typically, the reaction is incubated for 6 minutes at 25° C.

MLCK is assayed using the synthetic peptide substrate KKRPQRATSNVFS-$NH_2$, a thirteen amino acid fragment with a sequence corresponding to residues 11–23 of gizzard light chain except for a carboxy-terminal serine-$NH_2$ as described in Kemp, G. E., Pearson, R. B. and House, C. (1983) Proc. Nat. Acad. Sci. U.S.A. 80, pages 7471–7475. The standard assay is performed in a total volume of 100 microliters ($\mu l$) containing 20 mM Tri$_s$-HCl, pH 7.2, 10 mM $MgCl_2$, 100 uM [$\gamma$-$^{32}$P] ATP with a specific activity of 300–1000 counts per minute (cpm) per picomole (pmol), 50 $\mu M$ KKRPQRATSNVFS-$NH_2$, 0.02 $\mu g$ enzyme. Calmodulin was added at the concentrations indicated in the text and tables, and assays contained 1 mM EGTA or 1 mM EGTA plus approximately 200 $\mu M$ excess free calcium when calcium-dependent activity was measured. Calcium-independent activity is negligible in the calcium dependent gizzard enzyme. Assays are initiated by addition of adenosine triphosphate (ATP) and stopped by addition of 200 $\mu M$ HCl. Phosphate incorporated into the basic substrate is measured by spotting an aliquot on phosphocellulose filter paper, washing and counting the papers. The results are given in $IC_{50}$ values. An $IC_{50}$ indicates the dosage of compound in micromoles ($\mu M$) which inhibits MLCK by 50 percent. For example, an $IC_{50}$ of 25 indicates the compound at a dosage of 25 $\mu M$ inhibits the activity of MLCK by 50 percent. Results given in percentages (%) indicates the percent inhibition at a dosage of 100 $\mu M$.

EXAMPLES 16–30

| EXAMPLE NO. | COMPOUND | $IC_{50}$ ($\mu M$) |
| --- | --- | --- |
| 16 | 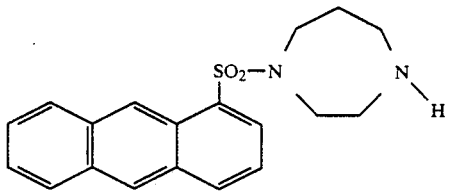 | 17 |

-continued

| EXAMPLE NO. | COMPOUND | IC$_{50}$ (μM) |
|---|---|---|
| 17 | | 50 |
| 18 | contains 35% of a new isomer, not stero chemically assigned. | 4.8 |
| 19 | | 11 |
| 20 | | 10 |
| 21 | | 100 |
| 22 | | 32 |
| 23 | | 65 |

-continued

| EXAMPLE NO. | COMPOUND | IC$_{50}$ ($\mu$M) |
|---|---|---|
| 24 | [phenanthridine with SO$_2$-N(diazocane)-H substituent] | 35 |
| 25 | [anthracene with SO$_2$-N(diazocane)-H substituent] | 5 |
| 26 | [phenanthrene with SO$_2$-N(diazocane)-H substituent] | 3.5 |
| 27 | [Br-fluorene-SO$_2$-N(diazocane)-N-H] | 76 |
| 28 | [Br-fluorene-SO$_2$-N(diazocane)-N-C(=NH)NH$_2$] | 55% |
| 29 | [Br-9,9-dimethylfluorene-SO$_2$-N(diazocane)-N-H] | 40% |

Antihypertensive Activity in Rats

The ability of the compounds of the present invention to lower blood pressure can be assessed in conscious spontaneously hypertensive rats (SHR). SHR (males) are purchased from Taconic Farms, Germantown, N.Y. and are approximately 16-17 weeks old when used to test the pharmacological effects. Rats, under ether anesthesia, receive a polyethylene tubing (PE50 fused to PE10) inserted via the caudal artery into the abdominal aorta to just below the renal arteries. This catheter is connected to a Spectromed pressure transducer and the direct arterial blood pressure is continuously recorded on an oscillographic recorder. Heart rate is determined via manual count of the pressure waves at a fast paper trace. In some instances where compounds are given intravenously, another catheter is positioned in the superior vena cava via the jugular vein. If drugs are administered orally, compounds are suspended in 0.4% aqueous methylcellulose and delivered via oral gavage with an oral feeding needle. Rats are fasted overnight prior to intravenous or oral tests. All incisions are closed and the rats are placed into plexiglass restrainers where they quickly regain consciousness. At least 90 minutes are allowed for the rats to fully regain consciousness and achieve stable blood pressures and heart rates.

Intravenously administered drugs are usually given as a rapid bolus. A comparable volume of solvent used to solublize the drug is used as a placebo treatment. In some cases drugs are given by constant intravenous infusion. The 0.4% aqueous methylcellulose is used as a placebo treatment for compounds given orally. Values are presented as the mean changes in mean blood pressure (MBP) in millimeters of mercury (mm Hg). Drug induced changes are compared with the changes in an appropriate placebo group. The compound is administered intravenously at a dosage of 1.0 to 5.0 milligrams per kilogram (mpk) body weight. The following results are representative for 1-((7-bromo-9H-fluoren-2-yl)sulfonyl)hexahydro-1H-1,4-diazepine from examples 4 and 27 (Compound A):

| Compound | Dosage (mpk) | Change in blood pressure (mm Hg) |
|---|---|---|
| Placebo | 0.0 | −5 |
| Compound (A) | 1.0 | −13 |
| | 2.5 | −25 |
| | 5.0 | −30 |

Compound A does not show activity upon oral administration at 50 mpk. The compound produces dose-dependent reduction in blood pressure upon intravenous administration. The magnitude of the effect at the highest dose studied (i.e. 5.0 mpk) represents a marked reduction compared with the placebo.

I claim:

1. A compound of the formula:

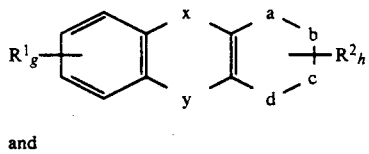
XIII and

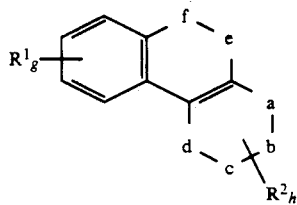
XIV or a pharmaceutically acceptable salt or solvate thereof, wherein $R^1$ and $R^2$ independently represents hydrogen, halogen, alkyl, hydroxyl, amino, alkenyl, substituted alkenyl, alkynyl, substituted alkynyl, aryl, substituted aryl, aralkyl, substituted aralkyl, heteroaryl, substituted heteroaryl, heteroaralkyl or substituted heteroaralkyl;

g and h independently represent 0, 1, 2, 3 or 4;

a, b, c, d, e, f, x and y independently represent —C= or —N= and x and y can further independently represent —O—, —S—, —NR$^{20}$— wherein R$^{20}$ represents hydrogen or alkyl, —CO— provided that only one of x or y can be —CO—, —(CR$^3$R$^4$)$_w$— or —(CR$^5$R$^6$)$_z$— wherein w and z can independently represent integers from zero to 8 inclusive and w+z is an integer from zero to 8 inclusive, and $R^3$, $R^4$, $R^5$ and $R^6$ independently represent
H,
alkyl,
substituted alkyl,
halogen,
—OH,
alkoxy,
thiol,
—COOH or salts, amides or esters thereof,
—NH$_2$, —NHR$^{31}$, —NR$^{31}$R$^{32}$ or —N$^+$R$^{31}$R$^{32}$R$^{33}$ wherein R$^{31}$R$^{32}$ and R$^{33}$ independently represent hydrogen or alkyl,
alkenyl,
alkynyl,
aryl,
aralkyl,
heteroaryl,
heteroaralkyl,
—COR$^{31}$ wherein R$^{31}$ is defined herein before,
—C(=NH)NR$^{31}$R$^{32}$ or salts thereof, wherein R$^{31}$ and R$^{32}$ are as defined hereinbefore;

wherein only one of a, b, c, d, e, f, x or y is

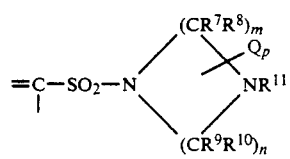

wherein $R^7$, $R^8$, $R^9$ and $R^{10}$ independently represent any of the values for $R^3$, $R^4$, $R^5$ and $R^6$, and m and n independently represent an integer from 2 to 3 inclusive, such that the sum of m+n=5;

p can be zero or one;

Q can be substituted for R$^{11}$ on the ring nitrogen or on the acylic nitrogen, or for any of R$^7$, R$^8$, R$^9$ or R$^{10}$ on the ring carbon, and can represent $-L_q-T_r-R^{12}$ wherein L represents —CO—, —COO—, CONR$^{21}$—, or —SO$_2$NR$^{21}$— wherein R$^{21}$ represents hydrogen or alkyl and q represents zero or one;

T represents a disubstituted unbranched or branched alkyl chain of zero to 10 carbon atoms which can optionally contain 1, 2 or 3 unsaturated bonds, disubstituted cycloalkyl of 3 to 10 carbon atoms, disubstituted cycloalkenyl of 3 to 10 atoms containing 1 or 2 unsaturated bonds, or disubstituted aryl, and r represents zero or one, and R$^{11}$ and R$^{12}$ independently represent any of the values for R$^3$, R$^4$, R$^5$, R$^6$, R$^7$, R$^8$ and R$^9$.

2. The compound of claim 1 wherein R$^1$ is hydrogen or halogen and g is 1, 2, 3 or 4.

3. The compound of claim 1 wherein R$^1$ is bromo, and g is 1, 2, 3 or 4.

4. The compound of claim 1 wherein R$^3$, R$^4$, R$^5$ and R$^6$ independently represent hydrogen or alkyl and w+z=1 or 2.

5. The compound of claim 1 wherein R$^3$, R$^4$, R$^5$ and R$^6$ independently represent hydrogen or methyl and w+z=1 or 2.

6. The compound of claim 1 wherein R$^7$, R$^8$, R$^9$ and R$^{10}$ independently represent hydrogen or alkyl.

7. The compound of claim 1 wherein R$^7$, R$^8$, R$^9$ and R$^{10}$ independently represent hydrogen.

8. The compound of claim 1 wherein R$^{11}$ represents hydrogen, —COR$^{31}$ or —C(=NH)NR$^{31}$R$^{32}$ wherein R$^{31}$ and R$^{32}$ independently represent hydrogen or alkyl.

9. The compound of claim 1 wherein $R^{11}$ represents hydrogen, $-COR^{31}$ or $-C(=NH)NR^{31}R^{32}$ wherein $R^{31}$ and $R^{32}$ represent hydrogen.

10. A compound according to claim 1 of the formula:

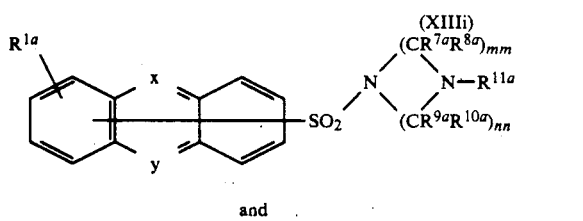

and

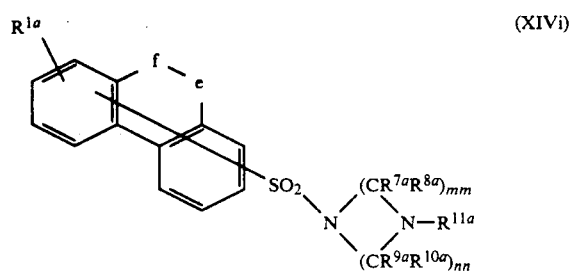

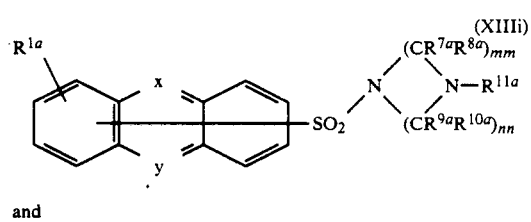

and

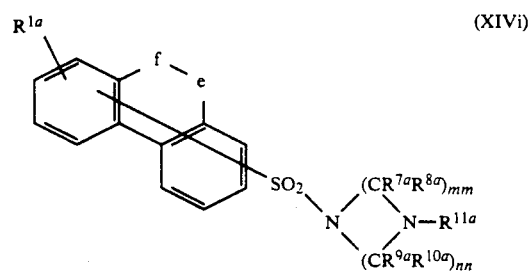

wherein $R^{1a}$ represents hydrogen or halogen, preferably bromo, e, f, x and y independently represent $-C=$, $-N=$, $-(CR^{3a}R^{4a})_w-$ or $-(CR^{5a}R^{6a})_z-$ wherein $R^{3a}$, $R^{4a}$, $R^{5a}$ and $R^{6a}$ independently represent hydrogen or alkyl, preferably hydrogen or methyl, and w and z independently represent 0, 1 or 2 and the sum of $w+z=1$ or 2; the sulfonate moiety ($-SO_2-$) can be substituted on any of the positions on the ring; and $R^{7a}$, $R^{8a}$, $R^{9a}$ and $R^{10a}$ independently represent hydrogen or alkyl, preferably hydrogen, mm+nn=5, and $R^{11a}$ independently represents hydrogen, $-COR^{31a}$ and $-C(=NH)NR^{31a}R^{32a}$ wherein $R^{31a}$ and $R^{32a}$ independently represent hydrogen or alkyl.

11. A compound selected from:
1-(9-Phenanthrenylsulfonyl)-hexahydro-1-H-1,4-Diazepine Hydrochloride; 1-(9-Anthracenylsulfonyl)-hexahydro-1H-1,4-Diazepine hydrochloride;
1-((9-bromo-2-phenanthrenyl)sulfonyl)hexahydro-1H-1,4-diazepine, hydrochloride;
1-(1-Anthracenylsulfonyl)hexahydro-1H-1,4-diazepine hydrochloride;
1-(2-Anthracenylsulfonyl)hexahydro-1H-1,4-diazepine hydrochloride;
1-((7-bromo-9H-fluoren-2-yl)sulfonyl)hexahydro-1H-1,4-diazepine, hydrochloride;
1-((7-bromo-9,9-dimethyl-9H-fluoren-2-yl)sulfonyl)-hexahydro-1H-1,4-diazepine hydrochloride;
4-((7-bromo-9H-fluoren-2-yl)sulfonyl)hexahydro-1H-1,4-diazepine-1-carboxaldehyde;
1-((7-bromo-9H-fluoren-2-yl)sulfonyl)hexahydro-4-methyl-1H-1,4-diazepine;
4-((7-bromo-9H-fluoren-2-yl)sulfonyl)hexahydro-1,1-dimethyl-1H-1,4-diazepinium iodide;
1-(2-Phenanthridinylsulfonyl)-hexahydro-1H-1,4-diazepine dihydrochloride;
1-(7-Phenanthridinsulfonyl)-hexahydro-1H-1,4-diazepine dihydrochloride;
1-(8-Phenanthridinsulfonyl)-hexahydro-1H-1,4-diazepine dihydrochloride
1-(1-Acridinylsulfonyl)-1H-1,4-diazepine dihydrochloride, hemihydrate;
1-((10,11-dihydro-5H-dibenzo(a,d)cycloheptene-2-yl)sulfonyl)-hexahydro-1H-1,4-diazepine hydrochloride, disodium chloride; and
1-((10,11-dihydro-5H-dibenzo(a,d)cycloheptene-3-yl)sulfonyl)-hexahydro-1H-1,4-diazepine hydrochloride, disodium chloride.

12. A pharmaceutical composition for treating hypertension containing an antihypertensive amount of a compound of formula XIII or XIV according to claim 1 in a pharmaceutically acceptable carrier.

13. A method for treating hypertension in a mammal comprising administering to a mammal in need of such treatment an antihypertensive effective amount of a compound of formula XIII or XIV:

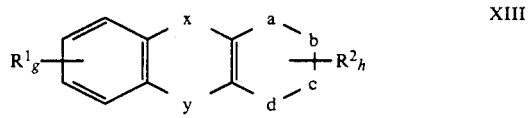

and

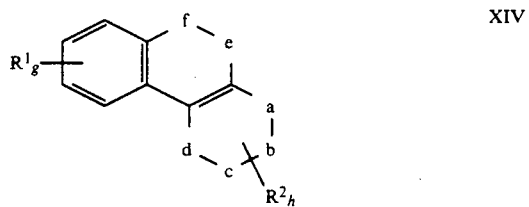

or a pharmaceutically acceptable salt or solvate thereof, wherein
$R^1$ and $R^2$ independently represents hydrogen, halogen, alkyl, hydroxyl, amino, alkenyl, substituted alkenyl, alkynyl, substituted alkynyl, aryl, substituted aryl, aralkyl, substituted aralkyl, heteroaryl, substituted heteroaryl, heteroaralkyl or substituted heteroaralkyl;
g and h independently represent 0, 1, 2, 3 or 4;
a, b, c, d, e, f, x and y independently represent $-C=$ or $-N=$ and x and y can further independently represent $-O-$, $-S-$, $-NR^{20}-$ wherein $R^{20}$ represents hydrogen or alkyl, $-CO-$, $-(CR^3R^4)_w-$ or $-(CR^5R^6)_z-$ wherein w and z can independently represent integers from zero to 8 inclusive and w+z is an integer from zero to 8 inclusive, and R$^3$, R$^4$, R$^5$ and R$^6$ independently represent H, alkyl, substituted alkyl, halogen, —OH, alkoxy, thiol, —COOH or salts, amides or esters thereof, —NH$_2$, —NHR$^{31}$, —NR$^{31}$R$^{32}$ or —N$^+$R$^{31}$R$^{32}$R$^{33}$ wherein R$^{31}$R$^{32}$ and R$^{33}$ independently represent hydrogen or alkyl, alkenyl, alkynyl, aryl, aralkyl, heteroaryl, heteroaralkyl, —COR$^{31}$ wherein R$^{31}$ is defined hereinbefore, —C(=NH)NR$^{31}$R$^{32}$ or salts thereof, wherein R$^{31}$ and R$^{32}$ are as defined hereinbefore; wherein at least one of a, b, c, d, e, f, x or y is

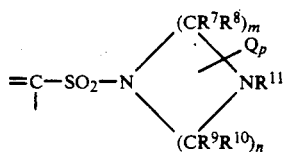

wherein
R$^7$, R$^8$, R$^9$ and R$^{10}$ independently represent any of the values for R$^3$, R$^4$, R$^5$ and R$^6$, and m and n independently represent an integer from 2 to 3 inclusive, such that the sum of
m+n=5;
p can be zero or one;
Q can be substituted for R$^{11}$ on the ring nitrogen or on the acylic nitrogen, or for any of R$^7$, R$^8$, R$^9$ or R$^{10}$ on the ring carbon, and can represent —L$_q$—T$_r$—R$^{12}$ wherein
L represents —CO—, —COO—, —CONR$^{21}$—, or —SO$_2$NR$^{21}$— wherein R$^{21}$ represents hydrogen or alkyl and q represents zero or one;
T represents a disubstituted unbranched or branched alkyl chain of zero to 10 carbon atoms which can optionally contain 1, 2 or 3 unsaturated bonds, disubstituted cycloalkyl of 3 to 10 carbon atoms, disubstituted cycloalkenyl of 3 to 10 atoms containing 1 or 2 unsaturated bonds, or disubstituted aryl, and r represents zero or one, and
R$^{11}$ and R$^{12}$ independently represent any of the values for R$^3$, R$^4$, R$^5$, R$^6$, R$^7$, R$^8$ and R$^9$.

* * * * *